(12) United States Patent
Pitulia

(10) Patent No.: US 7,874,977 B2
(45) Date of Patent: Jan. 25, 2011

(54) ANTI-STUTTERING DEVICE

(75) Inventor: Dan Pitulia, Västra Frölunda (SE)

(73) Assignee: Cochlear Limited, Lane Cove (AU)

( * ) Notice: Subject to any disclaimer, the term of this patent is extended or adjusted under 35 U.S.C. 154(b) by 0 days.

(21) Appl. No.: 10/589,363

(22) PCT Filed: Oct. 15, 2004

(86) PCT No.: PCT/SE2004/001481

§ 371 (c)(1),
(2), (4) Date: Aug. 14, 2006

(87) PCT Pub. No.: WO2005/037153

PCT Pub. Date: Apr. 28, 2005

(65) Prior Publication Data

US 2007/0010704 A1 Jan. 11, 2007

(30) Foreign Application Priority Data

Oct. 22, 2003 (SE) .................................. 0302774

(51) Int. Cl.
*A61F 5/58* (2006.01)
(52) U.S. Cl. ...................................................... 600/23
(58) Field of Classification Search ............. 600/23–24; 704/271; 128/897–898; 607/57
See application file for complete search history.

(56) References Cited

U.S. PATENT DOCUMENTS

| 3,566,858 | A | 3/1971 | Larson et al. |
| 4,221,488 | A | 9/1980 | Nunlist et al. |
| 4,498,461 | A | 2/1985 | Hakansson |
| 4,685,448 | A | 8/1987 | Shames et al. |
| 5,047,994 | A * | 9/1991 | Lenhardt et al. ............ 367/116 |
| 5,478,304 | A | 12/1995 | Webster |
| 5,961,443 | A | 10/1999 | Rastatter et al. |
| 2004/0032962 | A1* | 2/2004 | Westerkull ................... 381/151 |
| 2004/0172102 | A1* | 9/2004 | Leysieffer .................... 607/57 |

FOREIGN PATENT DOCUMENTS

| EP | 1 110 519 | 6/2001 |
| SE | 427418 A | 4/1983 |
| SE | 427418 B | 4/1983 |
| WO | WO 00/02418 A1 | 1/2000 |
| WO | WO 03/001845 A1 | 1/2003 |
| WO | WO 03/001846 A1 | 1/2003 |

OTHER PUBLICATIONS

Anders Tjellström, MD, PhD and Bo Håkansson, PhD; The Bone-Anchored Hearing Aid; Middle and Inner Ear Electronic Implantable Devices for Partial Hearing Loss; Otolaryngologic Clinics of North America; vol. 28, No. 1; Feb. 1995; pp. 53-72.
European Patent Office, "Communication Pursuant to Article 94(3) EPC," issued in connection with European Patent Application Serial No. 04 775 553.3, on Mar. 27, 2009 (3 pages).

(Continued)

*Primary Examiner*—Charles A Marmor, II
*Assistant Examiner*—Christine D Hopkins
(74) *Attorney, Agent, or Firm*—Kilpatrick Stockton LLP

(57) ABSTRACT

A device for treating and reducing stuttering by utilizing auditory feedback. A bone conducting hearing aid apparatus is arranged to be attached to the skull bone of a user with a stuttering problem so that his ear canal is left free. A tactile component in the form of a vibrator mechanically transmits sound information to the inner ears of the user via the skull bone so that both cochleas are stimulated. The cochlea on the opposite side of the skull receives a signal that is further delayed and also has another frequency characteristics compared to the digital received by the nearest cochlea.

18 Claims, 2 Drawing Sheets

OTHER PUBLICATIONS

European Patent Office, "Communication Pursuant to Article 96(2) EPC," issued in connection with European Patent Application Serial No. 04 775 553.3, on Nov. 19, 2009 (4 pages).

Patent Cooperation Treaty, "International Search Report," issued by the International Searching Authority in connection with PCT application No. PCT/SE2004/001481, mailed Jan. 21, 2005 (3 pages).

* cited by examiner

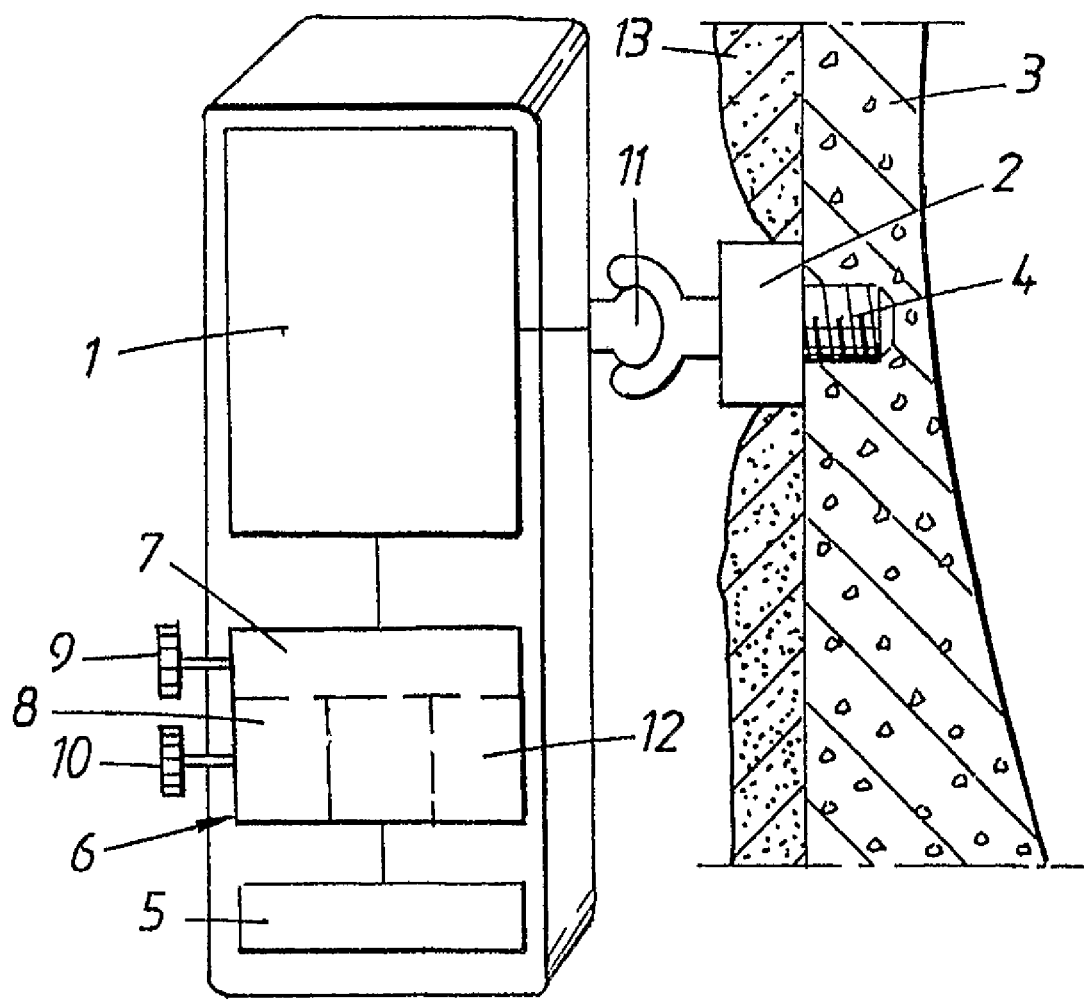

ANTI-STUTTERING DEVICE

CROSS-REFERENCE TO RELATED APPLICATIONS

This application claims priority to Swedish patent application 0302774-5 filed 22 Oct. 2003 and is the national phase under 35 U.S.C. §371 of PCT/SE2004/001481 filed 15 Oct. 2004.

FIELD OF THE INVENTION

The present invention relates generally to device for treating and reducing stuttering by means of auditory feedback.

BACKGROUND OF THE INVENTION

Stuttering is a speech deficiency which is characterised by certain interruptions or other voice problems in the speech flow, such as repetitions, prolongations and unintentional pauses in the speech. Approximately 1% of the adult population and 4% of the children suffer from stuttering. The reason for stuttering has not been fully explained, but it is probably caused by several different and interrelated factors. In one of the theories it is suggested that there is a conflict between the two hemispheres of the brain in such a way that the first, dominant hemisphere is disturbed by the second hemisphere of the brain. Then the brain signals to the muscles that produce speech is impaired so that stuttering is caused.

There are several different methods for the treatment of stuttering. Some of these methods might have been succesful for a short period of time, but they do not provide a satisfactory solution to the problem of stuttering. Modern speech therapy includes methods of psychological nature, such as methods for reducing the stutterers fearness for stuttering and avoidance but also methods for improving the stutterers self-confidence have been used. In main hospitals medically trained speech therapists are usually engaged in the treatment of speech and voice problems. Stuttering therapy is a hard and often arduous work, and it is certainly only a work in the long run.

It has been a main feature in almost all of these prior anti-stuttering methods to decrease the speech flow, but then hard training is required. For that reason there are different devices on the market which can be used for training slow speech. These devices are most often based on some type of auditory feedback by means of a microphone and headphones and they can be divided into three main categories:

Delayed Auditory Feedback (DAF)

Delayed auditory feedback (DAF) is based on a delay of the user's voice a fraction of a second between the microphone and the headphones. Typical delays are in the range of 50-200 ms. According to the theory this discrepancy is sensed by the brain so that the brain provides additional resources to the speech center resulting in a more fluent speech flow.

Frequency-Shifted Auditory Feedback (FAF)

Frequency-shifted auditory feedback (FAF) is based on a change of the frequency characteristics of the user's voice in the headphones so that the speech which is heard by the user is somewhat distorted. A typical frequency shift could be around a half octave. It is supposed that the speech center in the brain is activated in a similar way as for the delayed auditory feedback.

Masked Auditory Feedback (MAF)

According to the so-called masked auditory feedback (MAF) a synthetic sine signal is generated in the headphones. The frequency of this sine signal should correspond to the user's own phonetical frequency. In case of stuttering problems the signal is activated by the user himself and it is supposed that this signal then activates the speech center of the brain.

The most frequently used anti-stuttering devices are all based on delayed auditory feedback and these devices will therefore be described some more in detail here. These devices are supposed to be portable and they all comprise some type of headphones or earpieces in order to reproduce the voice of the user with some delay.

One example of such a device which comprises two headphones and at least one microphone which are connected to an amplifier is described in SE 427418. This device comprises a delay circuit in which the signal from the amplifier to one of the headphones is delayed compared to the other signal. This other, undelayed signal which is transmitted to one of the user's ears is sensed earlier by the dominant half of the brain so that the other half of the brain will not be able to induce stuttering according to the theory described in the patent.

The headphones are preferably made for permanent use and comprises a set of miniaturised earpieces of the type which can be inserted into the ear canal. The earpieces and the microphone are preferably connected into a single, portable unit for the user depending on his age and the intensity of his stuttering problems.

Other examples of anti-stuttering devices which are based on the delayed auditory feedback principle are disclosed in U.S. Pat. Nos. 3,566,858 4,685,448 5,478,304 5,961,443 and EP patent 1 110 519. These patents describe different solutions for the delay and frequency shift as well as techniques for picking up more of the user's voice compared to the surrounding sound.

A disadvantage with the described anti-stuttering devices is the fact that they are blocking the ear canal of the user. This in turn depends on the fact that the auditory-feedback is based on the principle that the sound is amplified and fed into the auditory meatus and stimulates the eardrum from the outside, i e a traditional air-conducting hearing aid principle. In order to prevent acoustic feedback problems in these devices, the auditory meatus is almost completely plugged by a hearing plug or by the hearing aid device itself. This causes the user a feeling of pressure, discomfort, and sometimes even eczema. In some cases it even causes the user problems like running ears due to chronic ear inflammations or infections in the auditory canal.

Another disadvantage with this type of device is the fact that it must be removed when it is not used as an anti-stuttering aid. If the device should be remained in the auditory meatus when the person is not talking, but only listening, it is blocking sound from the surroundings. However, a person with stuttering problems has normally no hearing problems and he does not need the device as a hearing aid in this case.

SUMMARY OF THE INVENTION

Therefore, there is a need for an anti-stuttering device which does not have the above-mentioned inconveniences and it is an object of this invention to provide an anti-stuttering device which is based on another type of hearing aid feedback. Instead of headphones and traditional, air-conducting hearing aid feedback the invention is based on the so-called bone-conducting hearing aids in which the ear canal is left free.

For persons who cannot or do not want to use traditional, air conducting hearing aids due to the above-mentioned problems there are other types of sound transmitting hearing aids on the market in which the ear canal is left free, i e bone conducting hearing aids which mechanically transmit the sound information to a persons inner ear via the skull bone by means of a vibrator. These bone conducting hearing aids could be of the type "traditional" bone conduction or they could be connected to an implanted titanium screw installed in the bone behind the external ear, direct bone conduction. In both cases the sound is transmitted via the skull bone to the cochlea (inner ear), i e the hearing aid works irrespective of a disease in the middle ear or not.

This type of hearing aid device based on direct bone conduction has been a revolution for the rehabilitation of patients with certain types of impaired hearing. It is very convenient for the patient and almost invisible with normal hair styles. It can easily be connected to the implanted titanium fixture by means of a bayonet coupling or a snap in coupling. One example of this type of hearing aid device is described in U.S. Pat. No. 4,498,461 and it is also referred to the BAHA® bone anchored hearing aids marketed by Entific Medical Systems in Göteborg. Unexpectedly it has now been found that persons with stuttering problems (but with no hearing problems) have been helped by using BAHA® bone anchored hearing aids. The invention then relates to a completely new use of such a device.

Consequently, the anti-stuttering device according to this invention is generally characterised by a bone conducting hearing aid apparatus arranged to be attached to the skull bone so that the ear canal is left free and which comprises a tactile component in the form of a vibrator from which the sound information is mechanically transmitted to the inner ears of the user via the skull bone.

According to a preferred embodiment the apparatus is arranged to be mechanically anchored in the skull bone by means of osseointegration and generate vibrations which are transmitted through the skull bone to the inner ears of the user.

According to a further embodiment the frequency characteristics of the apparatus is adjustable.

According to still another embodiment the apparatus comprises a delay circuit, preferably also adjustable.

BRIEF DESCRIPTION OF THE DRAWINGS

In the following the invention will be described more in detail with respect to the accompanying drawings, in which FIG. 3 illustrates an embodiment in which the apparatus comprises delay means and frequency shifting means.

DETAILED DESCRIPTION OF EMBODIMENTS OF THE INVENTION

Figure 1:
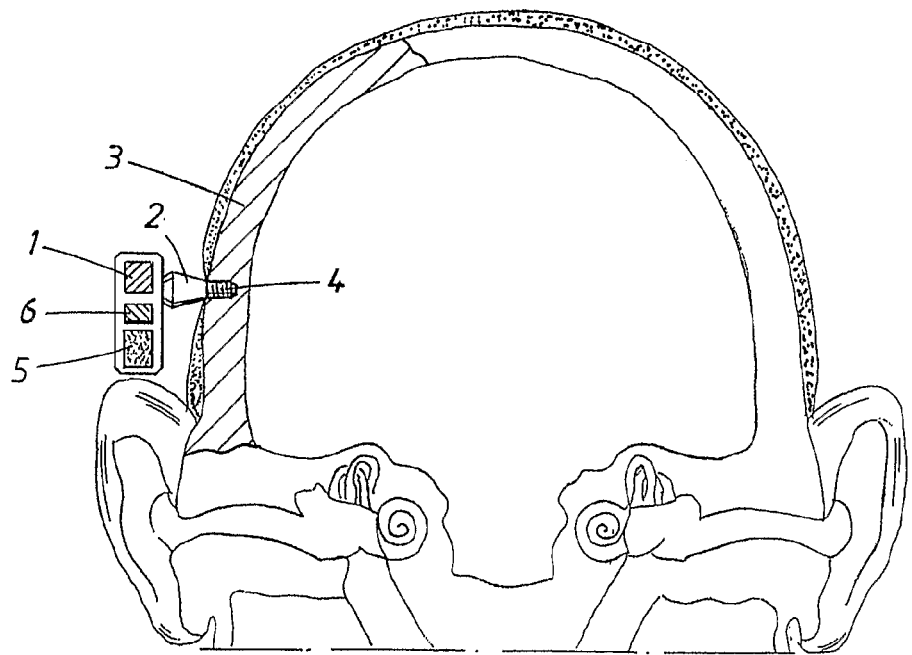
FIG. 1 illustrates the principles of the invention.

FIG. 1 illustrates schematically a person's skull with the auditory means in the form of an external ear, auditory meatus, middle ear and inner ear. The person has a stuttering problem but no hearing problem. A bone conducting hearing aid apparatus is anchored in the skull bone behind the external ear of a person, preferably in the mastoid bone. The hearing aid apparatus housing with a vibrator 1 which via a skin penetrating spacer 2 is mechanically anchored in the skull bone 3 by means of a fixture 4. The hearing aid apparatus is arranged to pick the apparatus housing which microphone signal then is amplified and filtered in an electrical circuit 6.

The vibrations which are generated by the vibrator 1 are transmitted through the skull bone to the nearest ear as well as to the other ear by bone conduction from one side of the skull to the other. By this bone conduction there is a certain delay before the vibrations reach the inner ear, cochlea, on the opposite side of the skull. It is supposed that it is this natural, "built-in" delay in the auditory feedback that explains why a stuttering person experiences a significant speech improvement by using a bone conducting hearing aid apparatus as anti-stuttering means. A significant difference between this invention and the previously known auditory feedback devices is the fact that both of the cochleas are stimulated so that the cochlea on the opposite side of the skull receives a signal which is further delayed compared to the signal to the nearest cochlea. Furthermore, this signal has other frequency characteristics compared to the signal received by the nearest cochlea.

Even if the bone conducting hearing aids might be used as they are, i e in the same condition as they are used for a conventional hearing aid apparatus for a person with impaired hearing, it is preferred to provide the electronic circuit 6 with analog to digital conversion means so that the analog signal from the microphone 5 is converted into a digital signal. Such a signal is more useful for signal processing. Preferably, the signal processing can be used for adapting for instance the frequency characteristics to the stuttering problematics. In the stuttering application it is a feedback and amplification of the person's own voice that is required, not the surrounding sound, as the stuttering person normally has no hearing problems. Then the frequency characteristics can be adapted for this specific case which is different from the hearing case. Signal processing can also be used for providing an additional delay in the auditory feedback if the internal delay should not be sufficient in the specific case. Also further frequency shifting circuitry (FAF) could be incorporated into the electronics. Such delay and frequency shift circuits are known per se and they will not be described in any detail here. In FIG. 3 it is schematically illustrated an apparatus having these additional functions. As already mentioned it should be important that in the anti-stuttering application the sound is transmitted not only to the nearest ear but also the other ear on the opposite side of the skull so that both of the cochleas are stimulated.

In order to suppress sound from other directions than from the forward direction, the microphone 5 in the hearing aid apparatus is preferably of the forward-directed, directional type.

Figure 2:
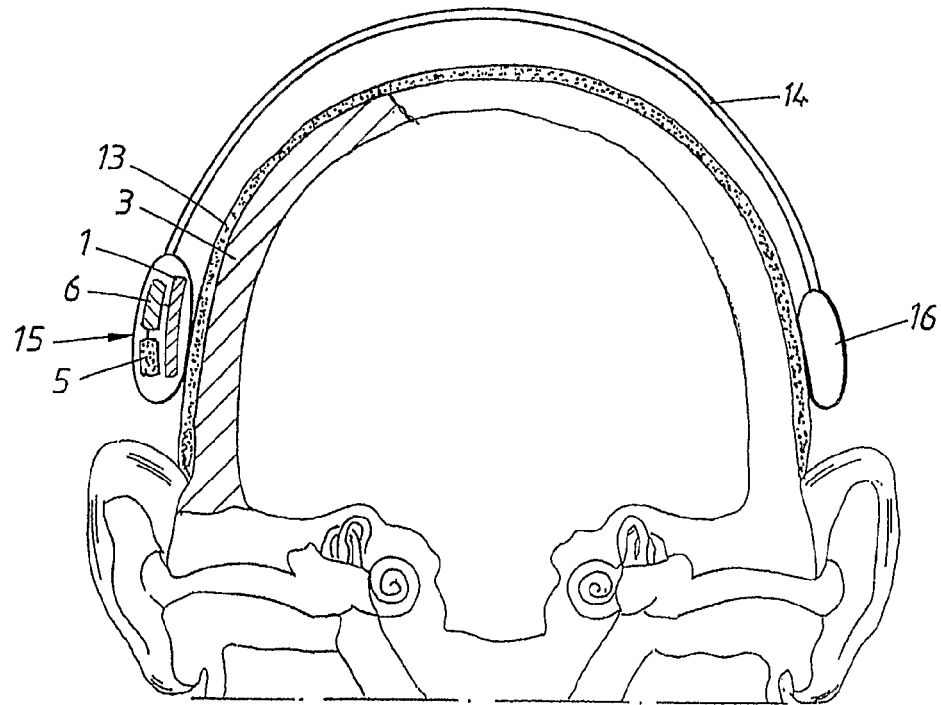
FIG. 2 illustrates an alternative embodiment of the invention.

Due to the efficient vibratory transmission without any damping, intermediate skin, it is expected that bone conducting hearing aids with skin penetration and a direct bone anchoring should give the best result in the treatment of stuttering. However, in some cases also a conventional bone conducting hearing aid apparatus of the type which is attached to the outer surface of the skin might be preferred, even if such an apparatus might cause the user a feeling of pressure or any other type of discomfort due to the pressure against the skin. However, an advantage with this type of apparatus is the fact that no surgical operation is required at all. As soon as the stuttering person has been cured and/or when he does not need the anti-stuttering device any more, then the treatment can be finished without any post operations required. In FIG. 2 it is illustrated such a conventional type of bone conducting hearing aid apparatus comprising a clamp 14 around the head and two small boxes 15, 16 attached against the skin 13 on the skull. One of the boxes includes the microphone 5, the electronic circuitry 6 and a vibrator 1 which mechanically transmits the sound information to the skull bone through the skin.

A common feature for both types of bone conducting devices is the fact that they are tactile, i e they include a tactile component in the form of a vibrator which transmits the vibrations to the skull bone. This is probably one of the reasons why these devices have such a good effect on the treatment of stuttering. The previously used auditory feedback devices have all been based on air conducting feedback through the auditory meatus. However, U.S. Pat. No. 4,685,448 is based on a tactile principle but in this case the vibrator is attached to the neck of the user in order to stimulate the vocal cord instead of cochlea as in our case, i e a vocal tactile feedback principle.

FIG. 3 illustrates, again, the principle for a conventional, direct bone conducting hearing aid apparatus, but in this case the electronics 6 comprises delaying and frequency shifting circuits, 7 and 8 respectively. Preferably the circuits are adjustable which has been indicated symbolically by means of adjusting knobs 9, 10. In the figure it is also illustrated a coupling device 11 as well as a power supply in the form of a battery 12.

The invention is not limited to the above-mentioned embodiments but can be varied within the scope of the accompanying claims.

The invention claimed is:

1. A method of treating stuttering, comprising:
    fitting a bone conducting hearing apparatus to a user having a stuttering problem but no substantial hearing impairment;
    receiving, with a microphone of the bone conducting hearing apparatus, sound including the user's voice; and
    directing the received user's voice back to the user through the bone conducting hearing apparatus, including:
        directing the received user's voice to a first cochlea and a second cochlea of the user, such that the received user's voice directed back to the user is received by the first cochlea before it is received by the second cochlea.

2. The method according to claim 1, wherein the received user's voice directed back to the user is directed back through vibration transmitted directly into the skull bone by physical attachment of the bone conduction hearing apparatus to the skull bone.

3. The method according to claim 1, further comprising:
    adjusting frequency characteristics of the bone conducting hearing aid apparatus.

4. The method according to claim 1, further comprising:
    further delaying directing back to the user the received user's voice.

5. The method according to claim 1, further comprising:
    suppressing sound from directions other than a forward direction in front of the user.

6. The method according to claim 4, further comprising:
    adjusting the further delay.

7. The method according to claim 1, further comprising:
    shifting a frequency of the received voice of the user directed back to the user.

8. The method according to claim 1, further comprising:
    transmitting to each cochlea of the user sound information having different frequency characteristics.

9. The method of claim 1, further comprising amplifying the received user's voice more than the surrounding sound and directing the amplified received user's voice back to the user.

10. The method of claim 1, wherein the first cochlea and the second cochlea are both stimulated by the sound including the voice of the user through natural hearing.

11. A method of treating stuttering, comprising:
    fitting a bone conducting hearing apparatus to a user having a stuttering problem but no substantial hearing impairment;
    receiving, with a microphone of the bone conducting hearing apparatus, sound including a voice of the user; and
    directing the received user's voice back to the user through the bone conducting hearing apparatus to treat the stuttering problem so that a first cochlea and a second cochlea of the user are stimulated by the bone conducting hearing apparatus, wherein there is a delay in stimulating the first cochlea relative to the second cochlea.

12. The method of claim 11, wherein both the first cochlea and the second cochlea are also stimulated by the sound including the voice of the user through natural hearing.

13. The method of claim 11, wherein any delay in stimulating the first cochlea or the second cochlea relative to the stimulation of the first cochlea or the second cochlea, respectively, through natural hearing, is due solely to the bone conducting device.

14. The method of claim 11, further comprising amplifying the received user's voice more than the surrounding sound and directing the amplified received user's voice back to the user to treat the stuttering problem.

15. The method according to claim 11, wherein the received user's voice directed back to the user is directed back through vibration transmitted directly into the skull bone by physical attachment of the bone conduction hearing apparatus to the skull bone.

16. The method according to claim 11, further comprising:
    adjusting frequency characteristics of the bone conducting hearing apparatus.

17. The method according to claim 11, further comprising:
    further delaying directing back to the user the received user's voice.

18. The method according to claim 11, further comprising:
    shifting a frequency of the received voice of the user directed back to the user.

* * * * *